US00PP16597P2

(12) United States Plant Patent
Zaiger et al.

(10) Patent No.: US PP16,597 P2
(45) Date of Patent: May 30, 2006

(54) INTERSPECIFIC TREE NAMED: 'WESCOT'

(50) Latin Name: [*((Prunus armeniaca×(Prunus salicina×Prunus armeniaca))×Prunus salicina)×Prunus armeniaca*]
Varietal Denomination: Westcot

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 113 days.

(21) Appl. No.: 11/011,968

(22) Filed: Dec. 15, 2004

(51) Int. Cl.
*A01H 5/00* (2006.01)

(52) U.S. Cl. ..... Plt./180
(58) Field of Classification Search ..... Plt./180, Plt./184, 186
See application file for complete search history.

*Primary Examiner*—Anne Marie Grunberg
*Assistant Examiner*—June Hwu

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit ripening in the early maturity season of mid to late May.
2. Fruit with very good flavor and eating quality.
3. Heavy and regular bearer of fruit.
4. Fruit with an attractive orange flesh and skin color.
5. Relatively uniform ripening of fruit throughout the tree.
6. Fruit with good balance between acid and sugar.

1 Drawing Sheet

Botanical classification: [((*Prunus armeniaca*×(*Prunus salicina*×*Prunus armeniaca*))×*Prunus salicina*)×*Prunus armeniaca*].
Variety denomination: 'Wescot'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum and apricot trees, which are known to us, and mentioned herein, are 'Royal Zee' Plum (U.S. Plant Pat. No. 5,486), 'Red Beaut' Plum (U.S. Plant Pat. No. 2,539), 'PA7005-8' Apricot (U.S. Plant Pat. No. 7,034), and 'Tri-Gem' Apricot (U.S. Plant Pat. No. 6,755).

STATEMENT REGARDING FEDERALLY SPONSORED RESEARCH AND DEVELOPMENT

Not applicable.

ORIGIN OF THE VARIETY

The new and distinct variety of interspecific tree [((*Prunus armeniaca*×(*Prunus salicina*×*Prunus armeniaca*))×*Prunus salicina*)×*Prunus armeniaca*] was developed by us in our experimental orchard located near Modesto, Calif. as a first generation cross between our proprietary interspecific tree '58EF33' and 'PA7005-8' Apricot (U.S. Plant Pat. No. 7,034). The maternal parent '58EF33' was originated by us from crosses between the following proprietary selections and varieties; apricot '15W297', plumcot '4G1180', 'Red Beaut' Plum (U.S. Plant Pat. No. 2,539) and 'Royal Zee' Plum (U.S. Plant Pat. No. 5,486). A large number of these seedlings from this first generation cross were budded to older trees of 'Nemaguard' Rootstock (non-patented) to accelerate rapid fruit production for evaluation. Under close observation, one such seedling exhibited desirable fruit characteristics in the early maturity season and was selected in 2000 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of interspecific tree [((Apricot× Plumcot)×Plum)×Apricot] is large, vigorous, spreading in growth and a regular and productive bearer of large, freestone fruit with very good flavor and eating quality. The fruit is further characterized by holding firm on the tree after maturity (shipping ripe) for 7 to 10 days, being relatively uniform in size and ripening throughout the tree with an attractive orange skin and flesh color. The tree has a winter chilling requirement of approximately 500 hours at or below 45° F. In comparison to the apricot tree 'Tri-Gem' (U.S. Plant Pat. No. 6,755), the new variety is larger in size, has higher colored orange flesh and skin color and is approximately 7 days earlier in maturity. In comparison to the apricot parent 'PA7005-8' (U.S. Plant Pat. No. 7,034), the new variety is similar in size, skin and flesh color and is approximately 21 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, pruned in height at maturity to 3 to 3.5 meters for economical harvesting of fruit. The spread varies depending on cultural practice and average about 8'.

*Vigor.*—Vigorous, tree growth of 1.5 to 2 meters in height the first growing season. Varies with fertility, type of soil and cultural practices.

*Form.*—Spreading, crotch angle approximately 37°, angle increases with heavy crop load.

*Branching habit.*—Spreading, usually pruned to vase shape to allow more sunlight and air movement to center of tree to enhance fruit color and health of fruit spurs.

*Productivity.*—Productive, normal fruit thinning and spacing necessary for desired market size fruit set. Varies with climatic conditions during blooming period.

*Bearer.*—Regular, adequate fruit set 4 consecutive years. No alternate bearing observed.

*Fertility.*—Believed to be partially self fertile, poor set under bags with no other pollen. Pollinator recommended.

*Density.*—Medium dense, controlled by pruning.

*Hardiness.*—Hardy in all stone fruit growing areas of California. Winter chilling requirement approximately 500 hours at or below 45° F. Tree grown in USDA Hardiness Zone 9.

Trunk:

*Size.*—Medium. Average circumference 48.9 cm at 20.3 cm above ground on a 6 year old tree.

*Stocky.*—Medium stocky.

*Texture.*—Medium shaggy, gets rougher with age.

*Color.*—Varies from 7.5YR 6/2 to 7.5YR 5/2.

Branches:

*Size.*—Medium. Average circumference 15.4 cm at 1.1 meters above ground.

*Surface texture.*—New growth relatively smooth. Mature growth medium rough.

*Lenticels.*—Average number of 22 in a 25.8 square cm surface of branch. Large. Average length 4.4 mm. Average width 1.3 mm. Color varies from 7.5YR 7/6 to 10YR 8/6.

*Color.*—New growth varies from 10Y 6/6 to 2.5YR 3/6, varies with degree of direct sunlight. Mature growth varies from 5YR 3/4 to 7.5YR 3/4.

Leaves:

*Size.*—Medium to large. Average length 78.0 mm. Average width 65.0 mm.

*Form.*—Ovate.

*Apex.*—Cuspidate.

*Base.*—Obtuse.

*Margin.*—Serrulate.

*Thickness.*—Medium.

*Surface texture.*—Upper surface relatively smooth, slightly indented over midrib and leaf veins. Lower surface relatively smooth, small ridges created by midrib and pinnate venation. Both surfaces glabrous.

*Petiole.*—Size medium. Average length 33.2 mm. Average width 1.8 mm. Grooved longitudinally. Surface glabrous. Color varies from 5GY 7/4 on new leaves, turning 5R 2/8 as leaf matures.

*Glands.*—Reniform. Medium. Average length 0.8 mm. Average diameter 0.6 mm. Average number 2, varies from 1 to 3. Located primarily on upper portion of petiole and base of leaf blade. Color varies from 5GY 5/6 to 5GY 4/6.

*Color.*—Upper surface varies from 5GY 3/4 to 5GY 3/6. Lower surface varies from 5GY 5/4 to 5GY 3/6. Midvein color varies from 5GY 7/4 on new leaves, turning to 5R 4/6 on mature leaves.

Flower buds:

*Size.*—Medium. Average length 13.9 mm. Average diameter 8.2 mm.

*Hardiness.*—Hardy in all stone fruit growing areas of California.

*Form.*—Conical, becoming elongated before opening.

*Pedicel.*—Short. Average length 2.2 mm. Average width 1.7 mm. Color varies from 2.5GY 8/4 to 5GY 7/6.

*Color.*—Varies from 5RP 7/8 to 7.5RP 9/2.

*Number of buds per spur.*—Average 5, varies from 2 to 9.

Flowers:

*Size.*—Medium to large. Average height 15.0 mm. Average diameter 25.9 mm.

*Petals.*—Number — 5, alternately arranged to sepals. Size — medium. Average length 13.2 mm. Average width 14.2 mm. Form — orbicular. Margin — sinuate. Both surfaces glabrous. Color varies from 7.5RP 9/2 to 10RP 9/2.

*Sepals.*—Number — 5, alternately arranged to petals. Shape — triangular, apex pointed. Margin — entire. Size — medium. Average length 6.3 mm. Average width 5.1 mm. Color — upper surface varies from 10Y 6/6 to 5R 3/8. Lower surface varies from 2.5R 3/8 to 5R 2/8. Both surfaces glabrous.

*Stamens.*—Average number per flower — 29. Filament — average length 10.2 mm. Filament color N 9.5/. Anther color varies from 5Y 8/10 to 7.5Y 8/8.

*Pollen.*—Present. Very little set under bag. Believed to be only partially self fertile, pollinator recommended. Color varies from 2.5Y 7/8 to 5Y 7/10.

*Pistil.*—Usually 1, varies from 1 to 2. Surface — pubescent. Average length 11.7 mm. Average height compared to stamens, 1.3 mm below anthers. Color varies from 10Y 9/4 to 10Y 8.5/6.

*Fragrance.*—Heavy aroma.

*Blooming period.*—Date of First Bloom Feb. 25, 2003. Date of Petal Fall Mar. 4, 2003, varies with climatic conditions.

*Color.*—Varies from 7.5RP 9/2 to 10RP 9/2, fades with age of flower.

*Number flowers per flower bud.*—Average 2, varies from 1 to 3.

*Pedicel.*—Average length 2.3 mm. Average width 1.9 mm. Color varies from 5GY 9/2 to 5GY 8/4.

Fruit:

*Maturity when described.*—Firm ripe.

*Date of first picking.*—May 21, 2003.

*Date of last picking.*—May 27, 2003, varies slightly with climatic conditions.

*Size.*—Large. Average diameter axially 61.9 mm. Average transversely in suture plane 58.6 mm. Average across suture plane 54.9 mm. Average weight 115.0 grams, varies slightly with fertility of the soil, amount of thinning and climatic conditions.

*Form.*—Nearly globose, slightly elongated and compressed in suture plane.

*Suture.*—Shallow, distinct, extends from base to apex.

*Ventral surface.*—Lipped, well sealed.

*Apex.*—Varies from rounded to slightly retuse.

*Base.*—Varies from flat to slightly retuse.

*Cavity.*—Nearly rounded to slightly elongated in suture plane. Average depth 5.6 mm. Average diameter 8.0 mm.

Stem:

*Size.*—Small. Average length 6.1 mm. Average diameter 3.2 mm.

*Color.*—Varies from 2.5GY 6/6 to 2.5GY 6/8.

Flesh:

*Ripens.*—Evenly.

*Texture.*—Firm.

*Fibers.*—Few, small, tender.

*Firmness.*—Firm, with greater firmness than most commercial apricots.

*Aroma.*—Slight, apricot aroma.

*Amydgalin.*—Undetected.

*Eating quality.*—Very good.

*Flavor.*—Very good, good balance between acid and sugar.

*Juice.*—Moderate, enhances flavor.

*Brix.*—Average 16.1°, varies slightly with amount of fruit per tree and climatic conditions.

*Color.*—Varies from 6.25YR 7/14 to 6.25YR 7/12. Pit cavity varies from 6.25YR 6/12 to 5YR 6/12.

Skin:

*Thickness.*—Medium.

*Surface.*—Smooth.

*Down.*—Moderate amount, very short.

*Tendency to crack.*—None.

*Color.*—Varies from 5YR 6/10 to 5YR 5/12, surface exposed to direct sunlight varies from 10R 5/12 to 10R 5/14.

*Tenacity.*—Tenacious to flesh.

*Astringency.*—Very slight to none.

Stone:

*Type.*—Freestone.

*Size.*—Large. Average length 31.8 mm. Average width 24.8 mm. Average thickness 13.4 mm.

*Form.*—Ovoid.

*Base.*—Flat.

*Apex.*—Very slightly pointed. Average length 0.2 mm.

*Surface.*—Slightly pitted throughout, pit cavities vary from round to elongated. Very shallow, narrow furrows starting at base extending toward apex for short distances. Two narrow furrows on each side of suture extending from base to apex.

*Sides.*—Varies from equal to unequal with one side extending further from suture plane.

*Ridges.*—One small, narrow ridge on each side of stone created by furrows near the suture, extending from base to apex.

*Tendency to split.*—None.

*Color.*—Varies from 7.5YR 6/4 to 10YR 5/4 when dry.

Kernal:

*Form.*—Ovoid.

*Viability.*—Viable, complete embryo development.

*Size.*—Large. Average length 19.4 mm. Average width 13.8 mm. Average depth 6.6 mm.

*Skin.*—Color varies from 7.5YR 6/6 to 7.5YR 4/8 when dry.

Use: Dessert. Market — local and long distance.

Keeping quality: Good, held firm in cold storage 2 weeks at 38° to 42° F. without internal breakdown or appreciable loss of flavor.

Shipping quality: Good, minimal bruising of flesh or skin scarring during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, spreading growth and being a productive and regular bearer of large, freestone fruit with very good flavor and eating quality; the fruit is further characterized by having an attractive orange flesh and skin color, holding firm on the tree 7 to 10 days after maturity (shipping ripe) and being relatively uniform in size throughout the tree.

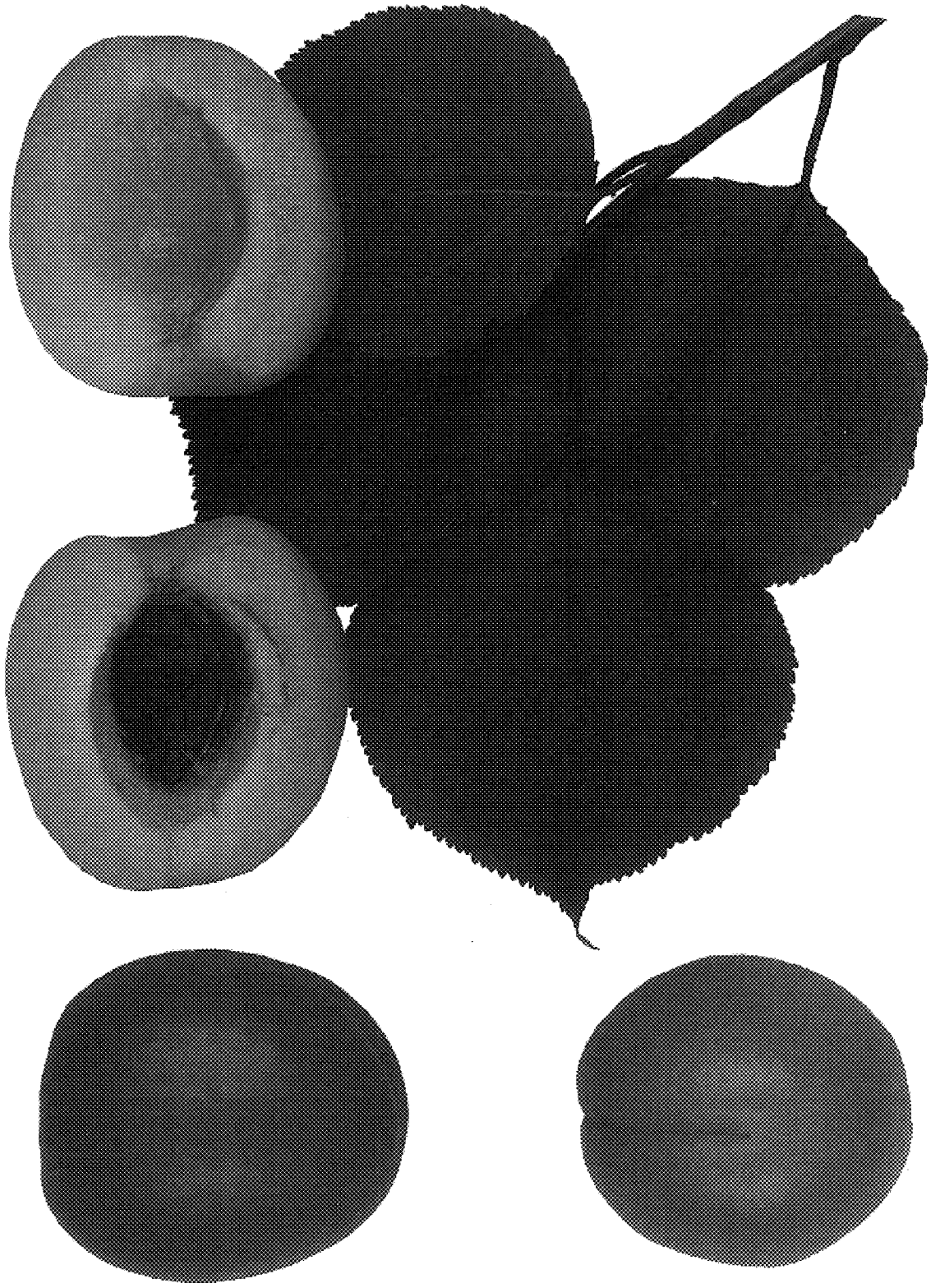

* * * * *